US010627497B2

(12) United States Patent
Chen et al.

(10) Patent No.: US 10,627,497 B2
(45) Date of Patent: Apr. 21, 2020

(54) CLUSTERING, NOISE REDUCTION AND VISUALIZATION METHOD FOR DOPPLER ULTRASOUND IMAGES

(71) Applicant: AMCAD BIOMED CORPORATION, Taipei (TW)

(72) Inventors: Argon Chen, Taipei (TW); Jia-Jiun Chen, Taipei (TW); Yu-Han Shen, Taipei (TW); Cheng-Hsien Liu, Taipei (TW)

(73) Assignee: AMCAD BIOMED CORPORATION, Taipei (TW)

( * ) Notice: Subject to any disclaimer, the term of this patent is extended or adjusted under 35 U.S.C. 154(b) by 611 days.

(21) Appl. No.: 15/388,435

(22) Filed: Dec. 22, 2016

(65) Prior Publication Data

US 2017/0184714 A1 Jun. 29, 2017

(30) Foreign Application Priority Data

Dec. 23, 2015 (TW) .............................. 104143257 A (51) Int. Cl.
*G01S 7/52* (2006.01)
*A61B 8/08* (2006.01)
(Continued)

(52) U.S. Cl.
CPC ............ *G01S 7/52077* (2013.01); *A61B 8/06* (2013.01); *A61B 8/08* (2013.01); *A61B 8/0891* (2013.01);
(Continued)

(58) Field of Classification Search
CPC .... G01S 7/52; G01S 15/8988; G01S 7/52053; G01S 7/52077; G01S 7/52071;
(Continued)

(56) References Cited

U.S. PATENT DOCUMENTS 5,279,302 A 1/1994 Tamano et al.
5,857,973 A 1/1999 Ma et al.
(Continued)

FOREIGN PATENT DOCUMENTS

JP H08173417 A 9/1993

OTHER PUBLICATIONS

European Extended Search Report and Search Opinion for corresponding EP Appln 16205350.8, dated Jun. 16, 2017.

*Primary Examiner* — Isam A Alsomiri
*Assistant Examiner* — Amie M Ndure
(74) *Attorney, Agent, or Firm* — Cantor Colburn LLP (57) ABSTRACT

The invention provides an analysis system for Doppler ultrasound image includes: a capture device, a processing device, and an output device. The capture device obtains a plurality of Doppler ultrasound images. The processing device arranges the color value in each pixel of the images based on the time domain, and obtains a reference sequence through a referencing method, furthermore performs a clustering method to obtain a plurality of correlation coefficient values, then uses a clustering and noise reducing method to classify into a primary pulsatile signal, a secondary pulsatile signal, and a noise signal, finally annotates the primary pulsatile signal, a secondary pulsatile signal, and a noise signal with different color values, respectively. The output device displays a plurality of visualized pulsatile ultrasound images for visualization.

14 Claims, 7 Drawing Sheets

| | Frame 1 | Frame 2 | Frame 3 | Frame 4 | ...... | Frame i | ...... | Frame I | |
|---|---|---|---|---|---|---|---|---|---|
| Pixel 1 | $B_{1,1}$ | $B_{1,2}$ | $B_{1,3}$ | $B_{1,4}$ | ...... | $B_{1,i}$ | ...... | $B_{1,I}$ | $C_1$ |
| Pixel 2 | $B_{2,1}$ | $B_{2,2}$ | $B_{2,3}$ | $B_{2,4}$ | ...... | $B_{2,i}$ | ...... | $B_{2,I}$ | $C_2$ |
| ...... | ...... | ...... | ...... | ...... | ...... | ...... | ...... | ...... | ... |
| ...... | ...... | ...... | ...... | ...... | ...... | ...... | ...... | ...... | ... |
| Pixel j | $B_{j,1}$ | $B_{j,2}$ | $B_{j,3}$ | $B_{j,4}$ | ...... | $B_{j,i}$ | ...... | $B_{j,I}$ | $C_j$ |

214

(51) Int. Cl.

| | | |
|---|---|---|
| *A61B 8/00* | (2006.01) | |
| *A61B 8/06* | (2006.01) | |
| *G01S 15/89* | (2006.01) | |
| *G06K 9/42* | (2006.01) | |
| *G06K 9/46* | (2006.01) | |
| *G06K 9/62* | (2006.01) | |

(52) U.S. Cl.
CPC .............. *A61B 8/468* (2013.01); *A61B 8/469* (2013.01); *A61B 8/488* (2013.01); *A61B 8/5207* (2013.01); *A61B 8/5223* (2013.01); *G01S 7/52053* (2013.01); *G01S 7/52071* (2013.01); *G01S 7/52074* (2013.01); *G01S 15/8988* (2013.01); *G06K 9/42* (2013.01); *G06K 9/4642* (2013.01); *G06K 9/4652* (2013.01); *G06K 9/4661* (2013.01); *G06K 9/623* (2013.01); *G06K 9/628* (2013.01); *G06K 9/6215* (2013.01); *G06K 9/6218* (2013.01); *A61B 8/463* (2013.01); *G01S 7/52036* (2013.01)

(58) Field of Classification Search
CPC ... G01S 7/52074; G01S 7/52036; G06K 9/42; G06K 9/46; G06K 9/62; G06K 9/623; G06K 9/6218; G06K 9/6215; G06K 9/628; G06K 9/4652; G06K 9/4642; G06K 9/4661; A61B 8/06; A61B 8/0891; A61B 8/468; A61B 8/469; A61B 8/488; A61B 8/5207; A61B 8/5223; A61B 8/08; A61B 8/463

See application file for complete search history.

(56) References Cited

U.S. PATENT DOCUMENTS

| | | | |
|---|---|---|---|
| 6,245,018 | B1 | 6/2001 | Lee |
| 2003/0181814 | A1 | 9/2003 | Ji et al. |
| 2005/0099887 | A1* | 5/2005 | Zimmerman ....... G01S 7/52003 367/12 |
| 2007/0025183 | A1* | 2/2007 | Zimmerman ....... G01S 7/52003 367/88 |
| 2010/0286522 | A1* | 11/2010 | Beach ................ A61B 5/02007 600/441 |
| 2013/0046168 | A1* | 2/2013 | Sui ...................... A61B 5/0035 600/411 |
| 2013/0184588 | A1 | 7/2013 | Palti |
| 2013/0345564 | A1 | 12/2013 | Nakaya et al. |

* cited by examiner

| | Frame 1 | Frame 2 | Frame 3 | Frame 4 | ...... | Frame i | ...... | Frame I | |
|---|---|---|---|---|---|---|---|---|---|
| Pixel 1 | $B_{1,1}$ | $B_{1,2}$ | $B_{1,3}$ | $B_{1,4}$ | ...... | $B_{1,i}$ | ...... | $B_{1,I}$ | $C_1$ |
| Pixel 2 | $B_{2,1}$ | $B_{2,2}$ | $B_{2,3}$ | $B_{2,4}$ | ...... | $B_{2,i}$ | ...... | $B_{2,I}$ | $C_2$ |
| ...... | ...... | ...... | ...... | ...... | ...... | ...... | ...... | ...... | ... |
| ...... | ...... | ...... | ...... | ...... | ...... | ...... | ...... | ...... | ... |
| Pixel j | $B_{j,1}$ | $B_{j,2}$ | $B_{j,3}$ | $B_{j,4}$ | ...... | $B_{j,i}$ | ...... | $B_{j,I}$ | $C_j$ |

CLUSTERING, NOISE REDUCTION AND VISUALIZATION METHOD FOR DOPPLER ULTRASOUND IMAGES

CROSS-REFERENCE TO RELATED APPLICATIONS

This application claims the benefit of priority based on Taiwan Patent Application No. 104143257 filed on Dec. 23, 2015, which is hereby incorporated by reference in its entirety.

BACKGROUND OF THE INVENTION

Field of the Invention

The invention relates to a method of Doppler ultrasound images clustering, noise reduction and visualization. In particular, a method implemented in an image processing system for Doppler ultrasound images.

Descriptions of the Related Art

Receiving of ultrasound images may be distinguished as power Doppler ultrasound image and color Doppler ultrasound image. Power Doppler ultrasound image shows complete artery and vein image, but it does not have direction information on blood flow. Nevertheless color Doppler ultrasound image only shows indirect direction information on blood flow. Otherwise, noise in the Doppler ultrasound images caused by the motion artifacts is also a critical problem for explaining the blood flow information. Thus, some patients should keep stationary during the Doppler examination because breathing may produce motion artifacts. Additionally, there are probe motion artifacts which may be arisen by using a hand-held probe (called a transducer) which is placed directly on and moved over the patient. Therefore, it is necessary to provide a suitable noise-reduced Doppler ultrasound image for evaluating the completely pulsatile information on blood flow.

In the prior art, Taiwan Patent No. 1275,383 in and U.S. Pat. No. 8,047,993 B2 disclose a non-invasive measurement method of tumor hemodynamic parameters to detect the degree of malignancy in tumors. The method comprises the steps of: using a power Doppler ultrasound unit to scan a tumor and capture sequential color images in a heartbeat cycle, and choosing an area of interest (AREA_ROI) from the images, labeling pixels reflecting signals of blood flow in the images during one heartbeat cycle to contour an area of tumor blood vessels (AREA_vessel); calculating a difference of PDVI between maximal systolic pressure and diastolic pressure during the heartbeat cycle to obtain tumor differential vascularity index (TDVI), in which PDVI is the ratio obtained by dividing pixels of AREA_vessel by total area in the section of AREA_ROI to determine the degree of malignancy by the TDVI. It can be applied to clinical diagnostic.

Furthermore, U.S. Pat. No. 8,047,993 B2 discloses a method for evaluation of renal perfusion with power Doppler ultrasonography. Serial renal vascular images at different vascular areas including the whole vascular tree, interlobar, arcuate, and interlobular vessels were captured. Imaging processing software was designed to analyze the changes of power Doppler intensity of colored pixels within regions of interest (ROI). Power Doppler Vascularity index (PDVI) has been defined as the percentage of vascular perfusion within a region of interest (ROI). The renal vascular perfusion index (RVPI) was defined as the maximal power Doppler vascular index which divided by minimal power Doppler vascular index (PDVI max/PDVI min) among the serial images. The mean of weighted power Doppler vascular index (WPDVI mean) was defined as the average of the intensity of colored pixels among the ROI within the serial images. By using the RVPI and WPDVI mean, a more dynamic sense of vascular perfusion and a novel approach for the evaluation of renal vascular function in clinical practice can be provided.

However, TW 1275383, U.S. Pat. Nos. 8,047,993 B2 and 8,777,860 B2 do not disclose clustering methods for evaluation of pulsatile information from blood flow in a sequence of power Doppler ultrasound images and the color Doppler ultrasound images. In particular, the present invention provides a method and system to quantify and classify the color pixels in the Doppler ultrasound images into three groups, namely the primary pulsatile signal, the secondary pulsatile signal, and noise signal based on the intensity changes of each color pixel over the sequence of Doppler ultrasound images. The classified signals will be visualized with different color values. Therefore, methods and systems in this invention provide the noise-reduced pulsatile signal images for reflecting pulsatile information form blood flow in the images, which is intended for vascular pulsatility analysis.

SUMMARY OF THE INVENTION

The present invention provides a system of clustering, noise reduction and visualization for Doppler ultrasound image. The Doppler ultrasound image processing system comprises a capture device, a processing device, and an output device, wherein the processing device further comprises a data conversion processor, a data analysis processor, and a data record processor.

The capture device obtains a plurality of Doppler ultrasound images based on a time domain, wherein each Doppler ultrasound image comprises a color value in each pixel.

The data conversion processor arranges each color value in each pixel of the Doppler ultrasound images based on the time domain to obtain a plurality of color value sequences.

The data analysis processor calculates the color value sequences through a referencing method to obtain a reference sequence, and compares the reference sequence with each color value sequences through a clustering method to obtain a plurality of correlation coefficient values, then classifies the color value sequences into a primary pulsatile signal, a secondary pulsatile signal, and a noise signal based on the correlation coefficient values through a clustering and noise reduction method.

The data record processor annotates the color values of the primary pulsatile signal, the secondary pulsatile signal, and the noise signal to obtain a plurality of visualized pulsatile ultrasound images.

The output device is connected to the processing device for displaying the visualized pulsatile ultrasound images.

In an embodiment of the invention, a method implemented in an image processing system of clustering, noise reduction and visualization for Doppler ultrasound image, which comprises: obtaining a plurality of Doppler ultrasound images based on time domain, wherein each Doppler ultrasound image comprises a color value in each pixel; and arranging each color value in each pixel of Doppler ultrasound images based on the time domain to obtain a plurality of color value sequences.

The method further comprises: calculating the color value sequences through a referencing method to obtain a reference sequence; comparing the reference sequence with each color value sequences through a clustering method to obtain a plurality of correlation coefficient values; using a clustering and noise reduction method to classify the color value sequences into a primary pulsatile signal, a secondary pulsatile signal, and a noise signal based on the correlation coefficient values; and annotating the color values of the primary pulsatile signal, the secondary pulsatile signal, and the noise signal to obtain a plurality of visualized pulsatile ultrasound images.

Other systems, methods, features, and advantages of the present invention will be or become apparent to one with skill in the art upon examination of following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DESCRIPTION OF THE PREFERRED EMBODIMENT

Having summarized various aspects of the present invention, reference will now be made in detail to the description of the disclosure as illustrated in the drawings. However, these embodiments are not intended to limit the present invention to any environment, applications, or implementations described in these embodiments. Therefore, description of these embodiments is only for purpose of illustration rather than to limit the scope of the present invention. It shall be appreciated that elements unrelated to the present invention are omitted from depiction in the following embodiments and the attached drawings.

The present invention discloses a method of clustering, noise reduction and visualization for Doppler ultrasound image. It should be noted that the method provides merely an example of the many different types of functional arrangements that may be employed to implement the operation of the various components of a system, a computer system, a multiprocessor computing device, and so forth. The execution steps of the present invention may include application specific software which may store in any portion or component of the memory including, for example, random access memory (RAM), read-only memory (ROM), hard drive, solid-state drive, magneto optical (MO), IC chip, USB flash drive, memory card, optical disc, or other memory components.

For some embodiments, the system comprises a capture device, a processing device, and an output device. The capture device is used to provide data such as image, text or control signals to the processing device such as a computer or other information appliance. The processing device performs data calculations, data comparisons, and data copying. Finally, the information from the analyzing system can be provided by the processing device and presented on the output device such as CRT monitors, LCD monitors and displays, gas plasma monitors, and televisions. The output device visually conveys text, graphics, and spectrum. Information shown on the output device is called soft copy because the information exists electronically and is displayed for a temporary period of time.

In accordance with some embodiments, the system further comprises of a storage medium and a memory. For example and without limitation, the storage medium can be a hard drive, an optical device or a remote database server coupled to a network, and storage software. The memory typically is the processor in which information is encoded, stored, and retrieved etc. The software can be stored in the memory and executed by the processing device when the computer system executes the method of clustering, noise reduction and visualization for Doppler ultrasound image.

Figure 1:
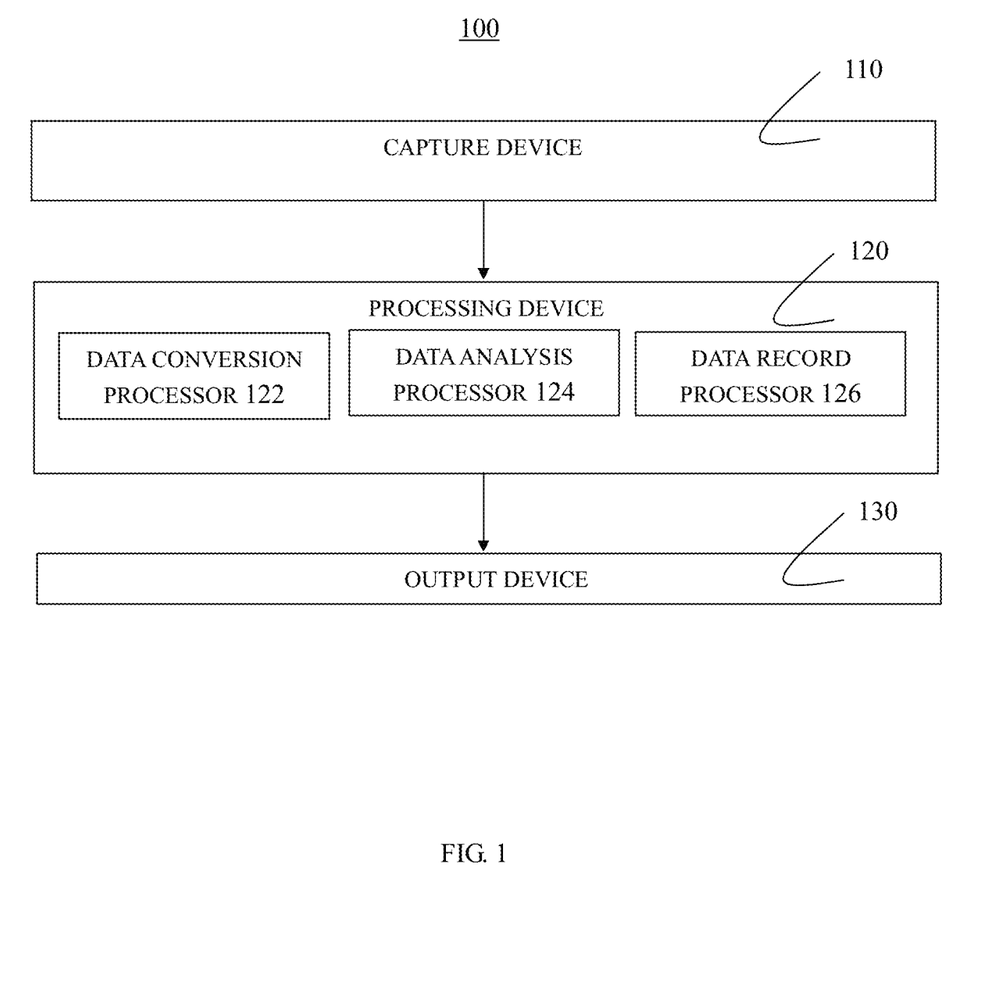
FIG. 1 is a block diagram of this system of clustering, noise reduction and visualization method for Doppler ultrasound image in accordance with various embodiments of the present invention.

FIG. 1 is a block diagram of a system 100 of clustering, noise reduction and visualization method for Doppler ultrasound image in accordance with various embodiments of the present invention. The Doppler ultrasound image processing system comprises a capture device 110, a processing device 120, and an output device 130. The processing device 120 includes a data conversion processor 122, a data analysis processor 124, and a data record processor 126.

Figure 2A:
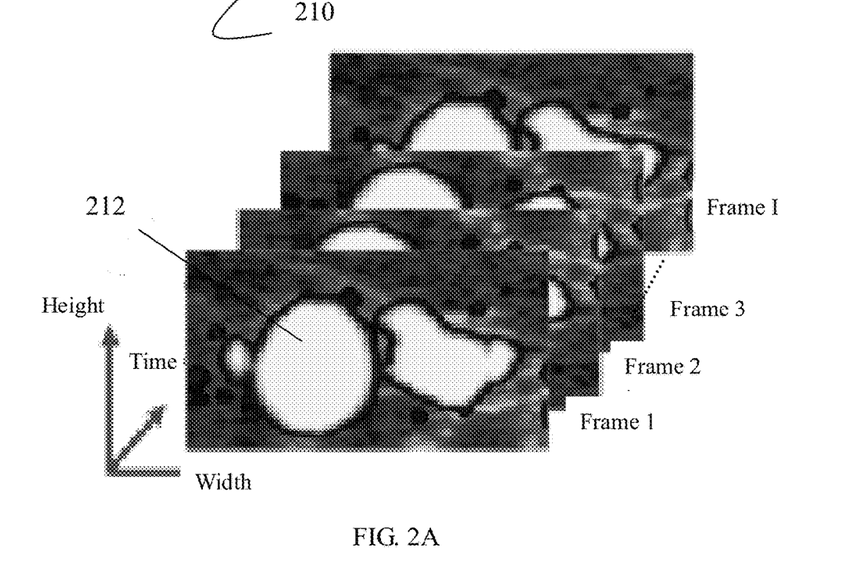
FIG. 2A illustrates a sequence of Doppler ultrasound images based on a time domain in accordance with various embodiments.
Figure 2B:
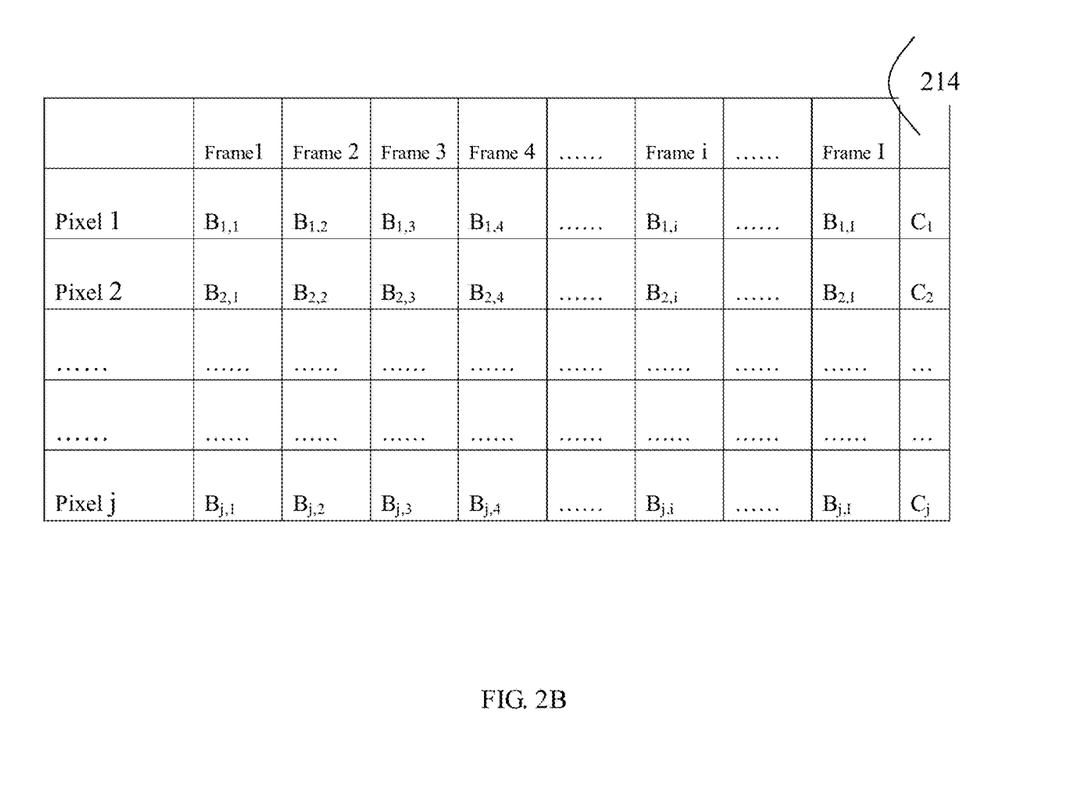
FIG. 2B illustrates an arrangement of a plurality of color value sequences based on a time domain in accordance with various embodiments.

Please refer to FIG. 2A and FIG. 2B together. FIG. 2A illustrates a sequence of Doppler ultrasound images in accordance with various embodiments. FIG. 2B illustrates an arrangement of a plurality of color value sequences based on a time domain in accordance with various embodiments. The capture device 110 acquires a plurality of Doppler ultrasound images (I frames) 210 based on a time domain, wherein each Doppler ultrasound image comprises a color value in each pixel ($B_{j,i}$) 212.

The data conversion processor 122 arranges the color value in each pixel (j=1~J) 212 of the Doppler ultrasound images based on the time domain (i=1~I) to obtain a plurality of color value sequences ($C_1, C_2, C_3, \ldots C_j$) 214. Each of the color value sequences is a sequences showing intensity change of the pixels. For various embodiments, the sequence showing intensity change of the pixels ($C_j$) is obtained according to the following expression:

$$C_j = \{B_{j,i}\}, i=1, 2, 3, \ldots, I \qquad \text{(Equation 1)}$$

wherein each $B_{j,i}$ of input data represents the intensity value of the $j^{th}$ pixel at the $i^{th}$ frame based on the definition of the intensity color map given by the original Doppler ultrasound image.

The data analysis processor 124 calculates the color value sequences through a referencing method to obtain a reference sequence ($C_{ref}$). The referencing method comprises an intensity percentage method, an average standard deviation ratio method, an autocorrelation method, a hierarchical correlation method or any combination thereof.

In one embodiment, the data analysis processor 124 performs the intensity percentage method to obtain the reference sequence. The intensity percentage method comprises the steps of: arranging the color value sequences ($C_1, C_2, C_3, \ldots C_j$) 214 according to the largest color value of each color value sequence to obtain a plurality of percentile ranks; choosing the color value sequences (j=1~J') which the percentile rank is within a predetermined rank range to obtain a reference group (R.G.); and averaging the color value sequences which the percentile rank belongs to the reference group to obtain the reference sequence. For various embodiments, the reference sequence is calculated according to the following expression:

$$C_{ref,} = \left\{ \frac{\sum_{j \in R.G.} B_{j,i}}{J'} \right\}, i = 1, 2, \ldots, I \qquad \text{(Equation 2)}$$

In another embodiment, the data analysis processor 124 performs the average standard deviation ratio method to obtain the reference sequence. The average standard deviation ratio method comprises the steps of: calculating the color value in each pixel of color value sequences (j=1~J) to obtain a plurality of standard ($Std_j$) values; and dividing the standard ($Std_j$) values by an average value of the standard values (Std Avg) to obtain a plurality of average standard deviation ratio (Avg STD ratio) values. The average standard deviation ratio value is calculated according to the following expression:

$$Avg\ STD\ \text{ratio} = \frac{Std_j}{Std\ Avg} = \frac{Std\ \text{of each}\ C_j}{\sum_{j=1}^{J} \frac{Std_j}{J}}, \forall j \qquad \text{(Equation 3)}$$

Then, the reference group is obtained by choosing the color value sequences which the averaging standard ration value is within a predetermined ration range, and the reference sequence is obtained by averaging the color value sequences from the reference group.

In another embodiment, the data analysis processor 124 performs the autocorrelation method to obtain the reference sequence. The autocorrelation method comprises the steps of: calculating each color value sequence through an autocorrelation function with a plurality of lag varieties to obtain a plurality of autocorrelation function values; and choosing a color value sequence which has the smallest autocorrelation value to obtain the reference sequence.

In another embodiment, the data analysis processor 124 performs the hierarchical correlation method to obtain the reference sequence. The hierarchical correlation method comprises the following steps of: (a) gathering the color value sequences into an $i^{th}$ reference sequence set, wherein an initial value of i is 1; (b) obtaining a plurality of correlation coefficient values of the $i^{th}$ reference sequence set by calculating each pair of the color value sequences in the $i^{th}$ reference sequence set through a correlation function; (c) selecting the pair of the color value sequences in the $i^{th}$ reference sequence set, which have a largest correlation coefficient value; (d) averaging the selected pair of the color value sequences in the $i^{th}$ reference sequence set to generate a new color value sequence; (e) gathering the new color value sequence and the color value sequences in the $i^{th}$ reference sequence set except for the selected pair of the color value sequences into a $(i+1)^{th}$ reference sequence set; (f) obtaining a plurality of correlation coefficient values of the $(i+1)^{th}$ reference sequence set by calculating each pair of the color value sequences in the $(i+1)^{th}$ reference sequence set through the correlation function; (g) determining whether all of the correlation coefficient values of the $(i+1)^{th}$ reference sequence set are less than a predetermined correlation threshold; and (h) when one of the correlation coefficient values of the $(i+1)^{th}$ reference sequence set is not less than the predetermined correlation threshold, setting i=i+1 and repeating steps (c), (d), (e), (f) and (g), and when the all of the correlation coefficient values of the $(i+1)^{th}$ reference sequence set are less than the predetermined correlation threshold, outputting the color value sequence in the $(i+1)^{th}$ reference sequence set which is generated by averaging a most number of the color value sequences in the first reference sequence set as a reference sequence.

For example, the data analysis processor 124 performs the hierarchical correlation method on the eight color value sequences $C_1, C_2, \ldots, C_8$ to obtain the reference sequence. First, the data analysis processor 124 gathers the eight color value sequences $C_1, C_2, \ldots, C_8$ into a $1^{st}$ reference sequence set. Next, the analysis processor 124 obtains the correlation coefficient values of the $1^{st}$ reference sequence set by calculating each pair of the color value sequences in the $1^{st}$ reference sequence set through the correlation function. On the assumption the pair of the color value sequences (i.e., $C_2$ and $C_3$) has the largest correlation coefficient value, the analysis processor 124 selects the pair of the color value sequences (i.e., $C_2$ and $C_3$) in the $1^{st}$ reference sequence set, which have the largest correlation coefficient value, and averages the color value sequences $C_2$ and $C_3$ to generate a new color value sequence $C'_{2,3}$. Next, the analysis processor 124 gathers $C'_{2,3}$ and the color value sequences $C_1, C_4, C_5, C_6, C_7, C_8$ into a $2^{nd}$ reference sequence set. Similarly, the analysis processor 124 obtains the correlation coefficient values of the $2^{nd}$ reference sequence set by calculating each pair of the color value sequences in the $2^{th}$ reference sequence set through the correlation function.

Afterwards, the analysis processor 124 determines whether all of the correlation coefficient values of the $2^{nd}$ reference sequence set are less than a predetermined correlation threshold. Assuming there is at least one of the correlation coefficient values of the $2^{nd}$ reference sequence set is not less than the predetermined correlation threshold, the analysis processor 124 selects the pair of the color value sequences in the $2^{nd}$ reference sequence set, which have a largest correlation coefficient value. Then, on the assumption the pair of the color value sequences ($C_1$ and $C'_{2,3}$) has the largest correlation coefficient value, the analysis processor 124 selects the pair of the color value sequences (i.e., $C_1$ and $C'_{2,3}$) in the $2^{nd}$ reference sequence set, which have the largest correlation coefficient value, and averages the pair of the color value sequences (i.e., $C_1$ and $C'_{2,3}$) to generate a new color value sequence $C'_{1,2,3}$.

Next, the analysis processor 124 gathers the new color value sequence $C'_{1,2,3}$ and the color value sequences $C_4$, $C_5$, $C_6$, $C_7$, $C_8$ into a $3^{rd}$ reference sequence set. Similarly, the analysis processor 124 obtains the correlation coefficient values of the $3^{rd}$ reference sequence set by calculating each pair of the color value sequences in the $3^{rd}$ reference sequence set through the correlation function, and determines whether all of the correlation coefficient values of the $3^{rd}$ reference sequence set are less than a predetermined correlation threshold. Assuming there is at least one of the correlation coefficient values of the $3^{rd}$ reference sequence set is not less than the predetermined correlation threshold, the analysis processor 124 selects the pair of the color value sequences in the $3^{rd}$ reference sequence set, which have a largest correlation coefficient value. Then, on the assumption the pair of the color value sequences (i.e., $C_5$ and $C_6$) has the largest correlation coefficient value, the analysis processor 124 selects the pair of the color value sequences (i.e., $C_5$ and $C_6$) in the $3^{rd}$ reference sequence set, which have the largest correlation coefficient value, and averages the pair of the color value sequences (i.e., $C_5$ and $C_6$) to generate a new color value sequence $C'_{5,6}$.

Next, the analysis processor 124 gathers the new color value sequence $C'_{5,6}$ and the color value sequences $C'_{1,2,3}$, $C_4$, $C_7$, $C_8$ into a $4^{th}$ reference sequence set. Similarly, the analysis processor 124 obtains the correlation coefficient values of the $4^{th}$ reference sequence set by calculating each pair of the color value sequences in the $4^{th}$ reference sequence set through the correlation function, and determines whether all of the correlation coefficient values of the $4^{th}$ reference sequence set are less than the predetermined correlation threshold.

On the assumption that all of the correlation coefficient values of the $4^{th}$ reference sequence set are less than the predetermined correlation threshold, the analysis processor 124 outputs the color value sequence $C'_{1,2,3}$ in the $4^{th}$ reference sequence set which is generated by averaging the most number (i.e., 3) of the color value sequences (i.e., $C_1$, $C_2$ and $C_3$) in the first reference sequence set as a reference sequence.

The data analysis processor 124 compares the reference sequence with each color value sequences through a clustering method to obtain the correlation coefficient values. The clustering method comprises a correlation grouping method, a grouping with lag-correlation method or a two-centers correlation clustering method or any combination thereof.

In an embodiment, the data analysis processor 124 performs the correlation grouping method to obtain the correlation coefficient values. The correlation grouping method comprises the step of: calculating each color value sequence with the reference sequence through a correlation function to obtain the correlation coefficient values of the color value sequences.

In another embodiment, the data analysis processor 124 performs the grouping with lag-correlation method to obtain the correlation coefficient values and the lag varieties. The grouping with lag-correlation method comprises the steps of: calculating each color value sequences with the reference sequence through a correlation function with a plurality of lag varieties to obtain a plurality of correlation coefficient values; and choosing the largest correlation coefficient value and the corresponding lag variety to obtain the correlation coefficient value and the lag variety of each color value sequence.

In another embodiment, the data analysis processor 124 performs the two-centers correlation clustering method to obtain a plurality of correlation coefficient values. The two-centers correlation clustering method comprises the following steps of: (a) gathering the color value sequences into an operation set; (b) calculating each of the color value sequences in the operation set with the reference sequence through a correlation function to obtain a plurality of temporary correlation coefficient values of the color value sequences; (c) removing the color value sequence with the smallest temporary correlation coefficient value from the operation set and assigning the smallest temporary correlation coefficient value to be the correlation coefficient value of the color value sequence with the smallest temporary correlation coefficient value; (d) removing the color value sequence with the largest temporary correlation coefficient value and assigning the largest temporary correlation coefficient value to be the correlation coefficient value of the color value sequence with the largest temporary correlation coefficient value; (e) updating the reference sequence by averaging the color value sequence with the largest temporary correlation coefficient value and the reference sequence; and (f) repeating steps (b), (c), (d), and (e) until all of the color value sequences are assigned with the correlation coefficient values.

For example, the data analysis processor 124 performs the two-centers correlation clustering method on the eight color value sequences $C_1$, $C_2$, ..., $C_8$ to obtain the plurality of correlation coefficient values. First, the data analysis processor 124 gathers the eight color value sequences $C_1$, $C_2$, ..., $C_8$ into an operation set. Next, the analysis processor 124 obtains a plurality of temporary correlation coefficient values of the color value sequences by calculating each of the color value sequences $C_1$, $C_2$, ..., $C_8$ in the operation set with the reference sequence through a correlation function. On the assumption the color value sequence $C_8$ has the smallest temporary correlation coefficient value and the color value sequence $C_2$ has the largest temporary correlation coefficient value. Thereafter, the analysis processor 124 removes the color value sequence $C_8$ from the operation set and assigns the smallest temporary correlation coefficient value to be the correlation coefficient value of the color value sequence $C_8$. Similarly, the analysis processor 124 removes the color value sequence $C_2$ from the operation set and assigns the largest temporary correlation coefficient value to be the correlation coefficient value of the color value sequence $C_2$. Afterwards, the analysis processor 124 update the reference sequence by averaging the color value sequence $C_2$ (which has the largest temporary correlation coefficient value) and the current reference sequence.

Next, the analysis processor 124 obtains a plurality of temporary correlation coefficient values of the color value sequences by calculating each of the color value sequences $C_1$, $C_3$, $C_4$, $C_5$, $C_6$, $C_7$ in the operation set with the updated reference sequence through the correlation function. On the assumption the color value sequences $C_3$ has the smallest temporary correlation coefficient value and the color value sequence $C_1$ has the largest temporary correlation coefficient value. Thereafter, the analysis processor 124 removes the color value sequence $C_3$ from the operation set and assigns the smallest temporary correlation coefficient value to be the correlation coefficient value of the color value sequence $C_3$. Similarly, the analysis processor 124 removes the color value sequence $C_1$ from the operation set and assigns the largest temporary correlation coefficient value to be the correlation coefficient value of the color value sequence $C_1$. Afterwards, the analysis processor 124 updates the reference sequence again by averaging the color value sequence $C_1$ (which has the largest temporary correlation coefficient value) and the current reference sequence.

Next, the analysis processor 124 obtains a plurality of temporary correlation coefficient values of the color value sequences by calculating each of the color value sequences ($C_4$, $C_5$, $C_6$, $C_7$) in the operation set with the updated reference sequence through the correlation function. On the assumption the color value sequence $C_4$ has the smallest temporary correlation coefficient value and the color value sequence $C_7$ has the largest temporary correlation coefficient value. Thereafter, the analysis processor 124 removes the color value sequences $C_4$ from the operation set and assigns the smallest temporary correlation coefficient value to be the correlation coefficient value of the color value sequence $C_4$. Similarly, the analysis processor 124 removes the color value sequence $C_7$ with the largest temporary correlation coefficient value from the operation set and assigns the largest temporary correlation coefficient value to be the correlation coefficient value of the color value sequence $C_7$.

Once again, the analysis processor 124 updates the reference sequence again by averaging the color value sequence $C_7$ (which has the largest temporary correlation coefficient value) and the current reference sequence. Afterwards, the analysis processor 124 obtains a plurality of temporary correlation coefficient values of the color value sequence by calculating the color value sequence ($C_5$, $C_6$) in the operation set with the updated reference sequence through the correlation function.

On the assumption the color value sequence $C_6$ has the smallest temporary correlation coefficient value and the color value sequence $C_5$ has the largest temporary correlation coefficient value. Thereafter, the analysis processor 124 removes the color value sequences $C_6$ from the operation set and assigns the smallest temporary correlation coefficient value to be the correlation coefficient value of the color value sequence $C_6$. Similarly, the analysis processor 124 removes the color value sequence $C_5$ from the operation set and assigns the largest temporary correlation coefficient value to be the correlation coefficient value of the color value sequence $C_5$. By the aforesaid operations all of the color value sequences ($C_1$, $C_2$, . . . , $C_8$) are assigned with their correlation coefficient values.

The data analysis processor 124 classifies the color value sequences into a primary pulsatile signal, a secondary pulsatile signal, and a noise signal based on the correlation coefficient values through a clustering and noise reduction method.

Figure 3:
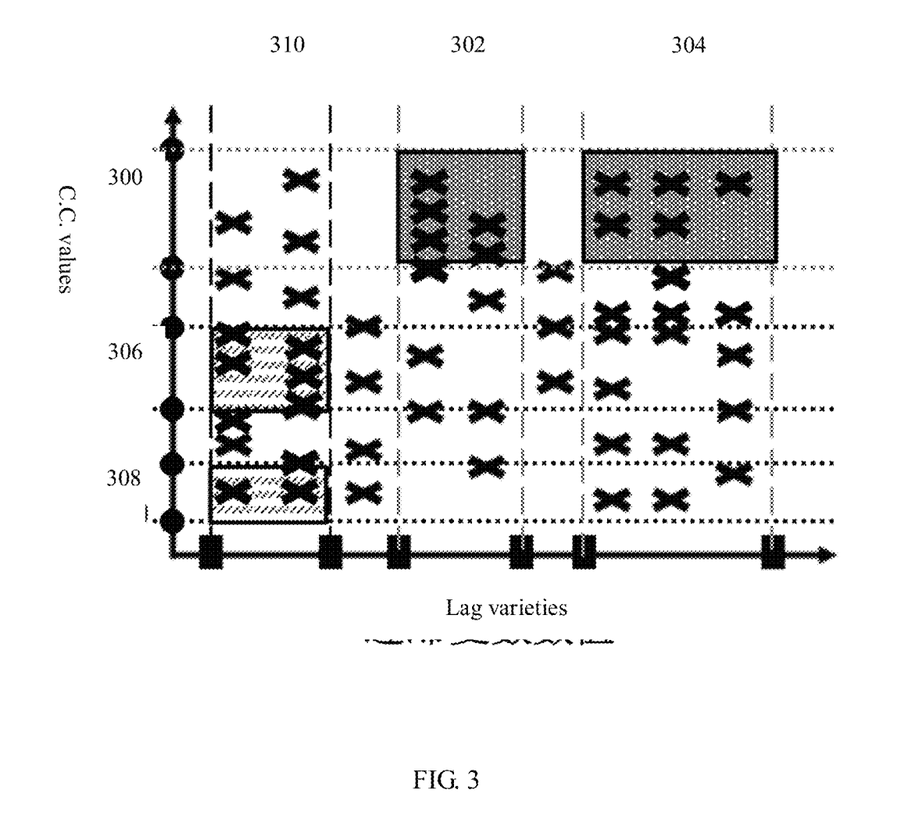
FIG. 3 illustrates a diagram for clustering and noise reduction method in accordance with various embodiments of the present invention.

FIG. 3 illustrates a diagram for clustering and noise reduction method in accordance with various embodiments of the present invention. The data analysis processor 124 performs the clustering and noise reduction method comprising the steps of: classifying the color value sequences into the primary pulsatile signal if the correlation coefficient value within a main correlation coefficient threshold 300 and the lag variety within a main lag-coefficient threshold 302, 304; and classifying the color value sequences into the secondary pulsatile signal if the correlation coefficient values within a secondary correlation coefficient threshold 306, 308 and the lag variety within a secondary lag-coefficient threshold 310. The data analysis processor 124 further classifies the remaining color value sequences into the noise signal.

Figure 4:
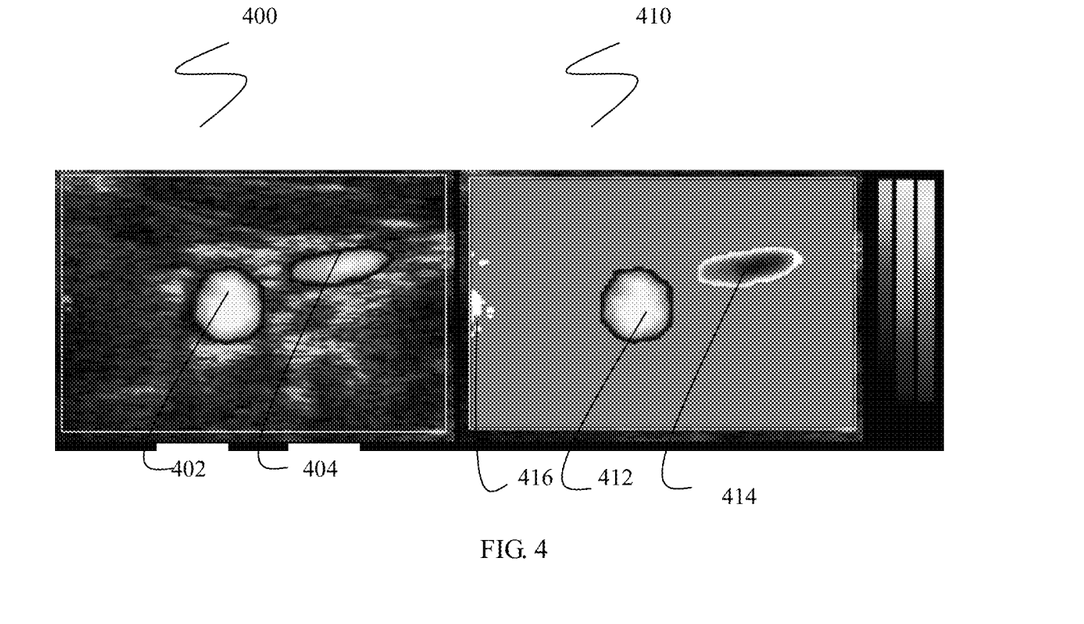
FIG. 4 illustrates common carotid artery and internal jugular vein in the original power Doppler ultrasound image and the corresponding visualized pulsatile ultrasound image in accordance with one embodiment of the present invention.

FIG. 4 illustrates common carotid artery 402 and internal jugular vein 404 in the original power Doppler ultrasound image 400 and the visualized pulsatile ultrasound images 410 in accordance with various embodiments of the present invention. The data analysis processor 124 performs the referencing method based on the combination of the intensity percentage and the average standard methods. The data analysis processor 124 further performs the clustering method based on the correlation grouping method, and then performs the clustering and noise reduction method.

The data analysis processor 124 chooses the color value sequences which the percentile rank is within a predetermined rank range, and chooses the color value sequences which the averaging standard ration value is within a predetermined ration range to obtain the reference group, wherein the predetermined rank range is less than 5% and predetermined ration range is less than 0.1. The data analysis processor 124 averages the color value sequences in the reference group to obtain the reference sequence.

The data analysis processor 124 classifies the color value sequences into the primary pulsatile signal 412 if the correlation coefficient value within a main correlation coefficient range, which is between 0.6 and 1.0, and classifies the color value sequences into the secondary pulsatile signal 414 if the correlation coefficient values within a secondary correlation coefficient threshold, which is between −1.0 and 0.4. The data analysis processor 124 further classifies the remaining color value sequences into the noise signal 416.

The data record processor 126 obtains a sequence of pulsatile ultrasound images 410 by classifying the color value sequences into three groups: the primary pulsatile signal, the secondary pulsatile signal, and the noise signal. The pixels of the primary pulsatile signal 412 in the visualized pulsatile ultrasound images 410 are displayed in first color values (e.g., warm colors from yellowish to dark red). The pixels of the secondary pulsatile signal 414 in the visualized pulsatile ultrasound images 410 are display in second color values (e.g., cold colors from light cyan to dark blue). The pixels of the noise signal are display in a third color value (e.g., a white color).

Figure 5:
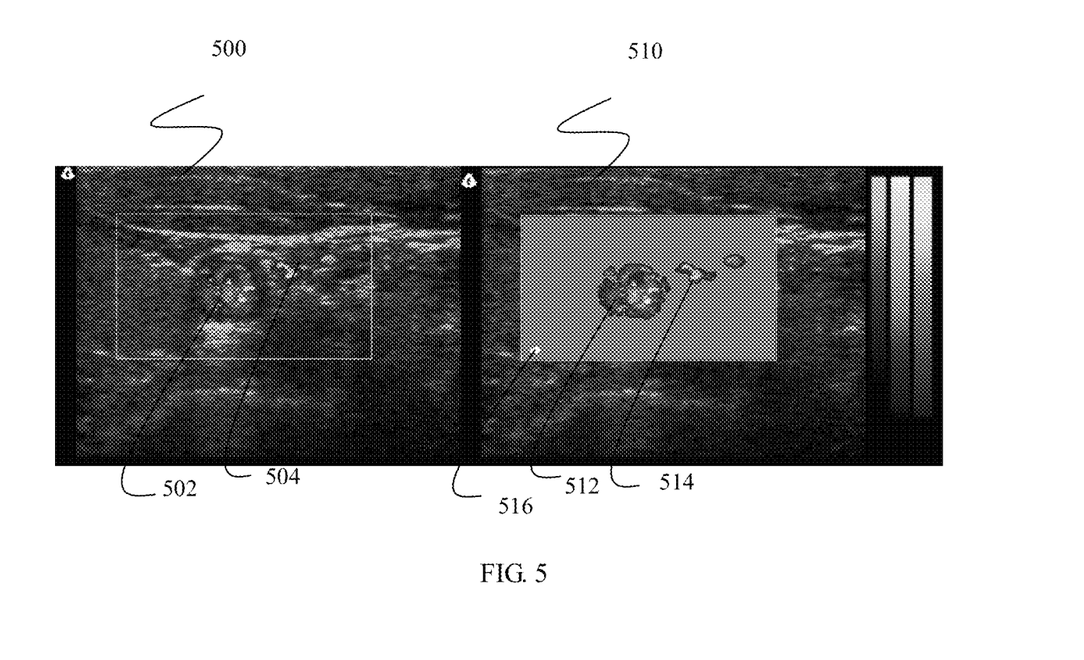
FIG. 5 illustrates common carotid artery and internal jugular vein in the original color Doppler ultrasound image and the corresponding visualized pulsatile ultrasound image in accordance with one embodiment of the present invention.

FIG. 5 illustrates common carotid artery 502 and internal jugular vein 504 in the original color Doppler ultrasound image 500 and the visualized pulsatile ultrasound image 510 in accordance with various embodiments of the present invention. The data analysis processor 124 performs the referencing method based on the combination of the intensity percentage method and the autocorrelation method. The data analysis processor 124 further performs the clustering method based on the two-centers correlation clustering method, and then performs the clustering and noise reduction method.

The data analysis processor 124 selects the plurality of color value sequences which the percentile rank is within a predetermined rank range, wherein the predetermined rank range is less than 10%. The plurality of color value sequences are calculated by the autocorrelation function calculation with lag varieties from 5 to 8. The data analysis processor 124 chooses the color value sequence which has the smallest autocorrelation function value to obtain the reference sequence.

Then, the data analysis processor 124 obtains a plurality of correlation coefficient values by calculating each color value sequence with the reference sequence through a correlation function. The data analysis processor 124 chooses the color value sequence with the smallest correlation coefficient value to obtain a minimum correlation coefficient value, and chooses the color value sequence with the largest correlation coefficient value to obtain a maximum correlation coefficient value.

The data analysis processor 124 averages the color value sequences which belong to the maximum correlation coefficient value and the reference sequence to obtain an updated reference sequence. Afterwards, the data analysis processor 124 obtains the correlation coefficient values of all color value sequence by calculate each remaining color value sequence with the updated reference sequence through the correlation function in sequence.

Furthermore, the data analysis processor 124 classifies the color value sequences into the primary pulsatile signal 512 if the correlation coefficient value within a main correlation coefficient threshold, wherein the main correlation coefficient threshold is between 0.6 and 1.0. The pixels of the primary pulsatile signal 512 in the visualized pulsatile ultrasound image are annotated by first color values (e.g., warm color values from light yellow to dark red).

The data analysis processor 124 classifies the color value sequences into the secondary pulsatile signal 514 if the correlation coefficient values within a secondary correlation coefficient threshold, wherein the secondary correlation coefficient threshold is between −1.0 and 0.4. The pixels of the secondary pulsatile signal 514 in the visualized pulsatile ultrasound image are annotated by second color values (e.g., cold color values from light cyan to dark blue).

The data analysis processor 124 classifies the remaining color value sequences into the noise signal 516 in a third color value (e.g., a white color). The data record processor 126 displays the visualized pulsatile ultrasound images 510 for visualization of the primary pulsatile signal 512, the secondary pulsatile signal 514 and the noise signal 516 based on clustering and noise reduction methods.

Figure 6:
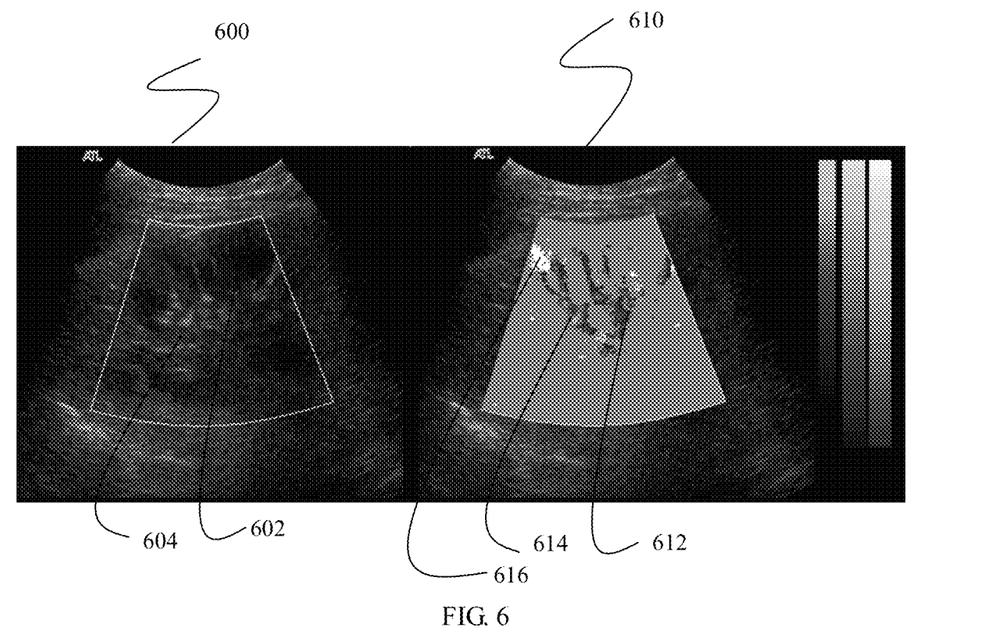
FIG. 6 illustrates renal artery and renal vein in the original power Doppler ultrasound image and the corresponding visualized pulsatile ultrasound image in accordance with one embodiment of the present invention.

FIG. 6 illustrates renal artery 602 and renal vein 604 in the original power Doppler ultrasound image 600 and the visualized pulsatile ultrasound images 610 in accordance with various embodiments of the present invention. The data analysis processor 124 performs the referencing method based on hierarchical correlation method to obtain the reference sequence, as aforementioned. Then, the data analysis processor 124 further performs the clustering method based on correlation grouping method to obtain the correlation coefficient values of the color value sequences by calculating each color value sequence with the reference sequence through a correlation function to obtain the correlation coefficient values.

Next, the data analysis processor 124 performs the clustering and noise reduction method as follows. The data analysis processor 124 classifies the color value sequences into the primary pulsatile signal 612 if the correlation coefficient value within a main correlation coefficient threshold, e.g., the main correlation coefficient threshold is between 0.6 and 1.0. The pixels of the primary pulsatile signal 612 in the visualized pulsatile ultrasound image are annotated by first color values (e.g. warm color values from yellowish to dark red) for showing the intensity changes of pixels.

The data analysis processor 124 classifies the color value sequences into the secondary pulsatile signal 614 if the correlation coefficient values within a secondary correlation coefficient threshold, e.g., the secondary coefficient threshold is between −1.0 to 0.2. The pixels of the secondary pulsatile signal 612 in the visualized pulsatile ultrasound image are annotated by second color values (e.g., cold color values from light cyan to dark blue) for showing the intensity changes of pixels.

The data analysis processor 124 classifies remaining color value sequences into the noise signal 616. The data record processor 126 displays the visualized pulsatile ultrasound images 610 for visualization of the primary pulsatile signal, the secondary pulsatile signal, and the noise signal based on clustering and noise reduction methods.

Figure 7:
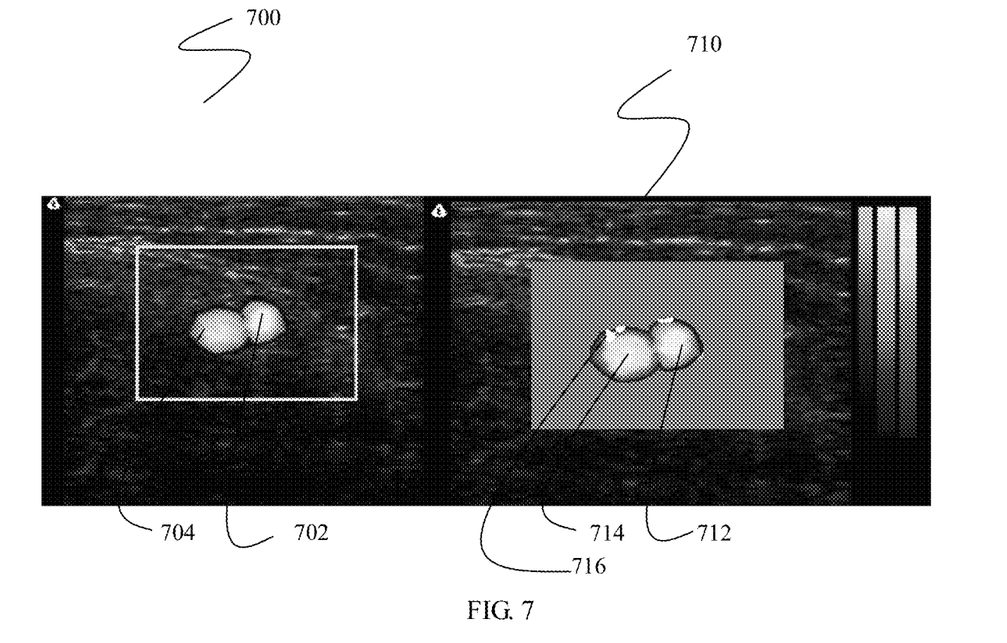
FIG. 7 illustrates brachial artery and brachial vein of arm in the original power Doppler ultrasound image and the corresponding visualized pulsatile ultrasound image in accordance with one embodiment of the present invention.

FIG. 7 illustrates brachial artery 702 and brachial vein 704 of arm in the original power Doppler ultrasound image 700 and the visualized pulsatile ultrasound image 710 in accordance with various embodiments of the present invention. The data analysis processor 124 performs the referencing method based on the combination of the intensity percentage method and the average standard deviation ratio method. The data analysis processor 124 further performs the clustering method based on the grouping with lag-correlation method, and then performs the clustering and noise reduction method.

The data analysis processor 124 arranges the color value sequences according to the largest color value of each of the color value sequences to obtain a plurality of percentile ranks. The data analysis processor 124 chooses the color value sequences which the percentile rank is within a predetermined rank range, and chooses the color value sequences which the averaging standard ration value is within a predetermined ration range to obtain the reference group, wherein the predetermined rank range is less than 5% and predetermined ration range is less than 0.1. The data analysis processor 124 averages the color value sequences in the reference group to obtain the reference sequence.

Then, the data analysis processor 124 performs the grouping with lag-correlation method to obtain the correlation coefficient values, and calculates each color value sequences with the reference sequence through a correlation function with a plurality of lag varieties to obtain a plurality of correlation coefficient values, wherein the range of the lag varieties are 0 to 8.

Furthermore, the data analysis processor 124 chooses the largest correlation coefficient value and the corresponding lag variety to obtain the correlation coefficient value and the lag variety of each color value sequence. The data analysis processor 124 classifies the color value sequences into the primary pulsatile signal 712 if the correlation coefficient value within a main correlation coefficient threshold and the lag variety within a main lag-coefficient threshold, e.g., the main correlation coefficient threshold is between −0.2 and 1.0 and the main lag-coefficient threshold is between 0 and 1. The pixels of the primary pulsatile signal 712 in the visualized pulsatile ultrasound image are annotated by first color values (e.g., warm color values from light yellow to dark red).

The data analysis processor 124 classifies the color value sequences into the secondary pulsatile signal 714 if the correlation coefficient values within a secondary correlation coefficient threshold and the lag variety within a secondary lag-coefficient threshold, e.g., the secondary correlation coefficient threshold is between −0.2 and 1.0 and the secondary lag-coefficient threshold is between 2 and 8. The pixels of the secondary pulsatile signal 714 in the visualized pulsatile ultrasound image are annotated by second color values (e.g. cold color values from light cyan to dark blue).

The data analysis processor 124 classifies remaining color value sequences into the noise signal 716. The data record processor 126 displays the visualized pulsatile ultrasound images 710 for visualization of the primary pulsatile signal 712, the secondary pulsatile signal 714 and the noise signal 716 based on clustering and noise reductions.

Figure 8:
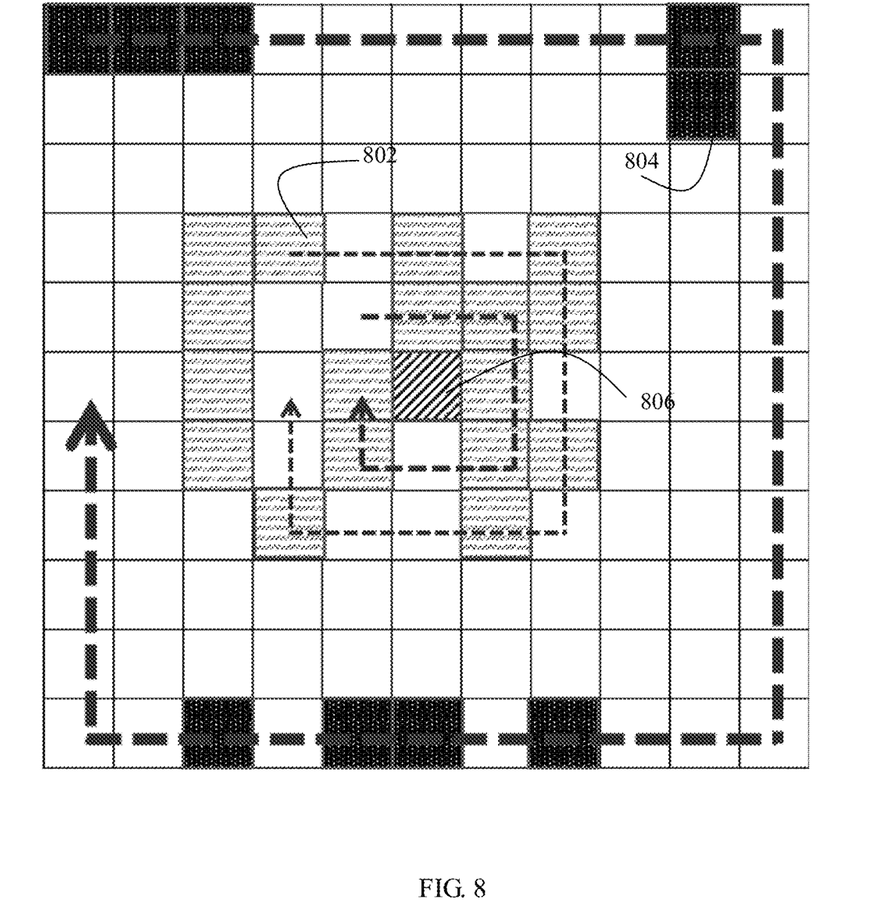
FIG. 8 illustrates a diagram for reclassifying the color values to obtain the visualized pulsatile ultrasound image in accordance with one embodiment of the present invention.

FIG. 8 illustrates a diagram for reclassifying the color values in the primary pulsatile signal and secondary pulsatile signal to obtain the visualized pulsatile ultrasound images (e.g., the visualized pulsatile ultrasound images 410 in FIG. 4) in accordance with various embodiments of the present invention. For each of the visualized pulsatile ultrasound images, the data record processor 126 selects a pixel of the noise signal 806 as a center pixel of a mask region, and starts at the center pixel and follows direction of arrow to search and calculate the number of pixels in the mask region of the visualized pulsatile ultrasound image.

Then, the data record processor 126 reclassifies the noise signal (i.e. center pixel) into the primary pulsatile signals 802 if the number of primary pulsatile signals is more than that of the secondary pulsatile signals in the mask region, and reclassifies the noise signal (i.e. center pixel) into the secondary pulsatile 804 if the number of secondary pulsatile signals is more than that of the primary pulsatile signals in the mask region.

The present invention provides a method and system to classify all pixels. In theory, the pixels from actual artifact interference are more likely to have a lower intensity and a random fluctuation. Therefore, the data record processor 126 will keep these pixels in the noise group, while, the remaining pixels (i.e. the pixels with a higher intensity and a periodical fluctuation) are to be reclassified to avoid misjudgment with a higher correlation coefficient threshold.

Figure 9:
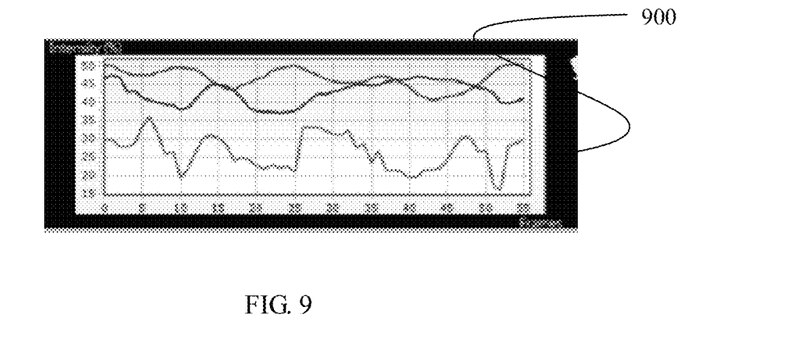
FIG. 9 illustrates intensity change value trends of the visualized pulsatile ultrasound image in accordance with one embodiment of the present invention.

FIG. 9 illustrates intensity value change trends of the visualized pulsatile ultrasound image in accordance with various embodiments of the present invention. As shown in Equation 4, the intensity value in each frame is expressed in percent.

$$\text{Intensity value} = \frac{\text{Sum of the normalized color values of the pixels}}{\text{the total number of the pixels}} \times 100(\%) \quad \text{(Equation 4)}$$

The data record processor 126 normalizes the color values of each pixel of the primary pulsatile signal, the secondary pulsatile signal, and the noise signal in the region of interest of the visualized pulsatile ultrasound image. Then, for color values of each pixel of the primary pulsatile signal in each frame (i.e., at each capture time), the data record processor 126 calculates the average of the normalized color values to obtain the intensity value in each frame. And, for color values of each pixel of the secondary pulsatile signal in each frame, the data record processor 126 calculates the average of the normalized color values to obtain the intensity value in each frame. Similarly, for color values of each pixel of the noise signal on each frame, the data record processor 126 calculates the average of the normalized color values to obtain the intensity value in each frame. Therefore, the intensity value change trends 900 of the primary pulsatile signal, the secondary pulsatile signal, and the noise signal are obtained.

In an embodiment, the data record processor 126 calculates a plurality of the first similarity indices ($SI_{ps}$) between the intensity value change trend of the primary signal and the intensity value change trend of the secondary pulsatile signal, the second similarity indices ($SI_{pn}$) between the intensity value change trend of the primary signal and the intensity value change trend of the noise signal, and the third similarity indices ($SI_{sn}$) between the intensity value change trend of the secondary signal and the intensity value change trend of the noise signal through a correlation function with a plurality of lag varieties, chooses the largest value from the first similarity indices ($SI_{ps}$) to be the pulsatile similarity index (PSI), chooses the largest value from the second similarity indices ($SI_{pn}$) and the similarity indices ($SI_{sn}$) to be the noise similarity index (NSI), and obtains a ratio coefficient (RC) by Equation 5 to assist evaluating the efficiency of visualization through outputting the ratio coefficient (RC) by the output device 130.

$$RC = \frac{NSI}{PSI} = \frac{\text{Max}(SI_{pn}, SI_{sn})}{\text{Max}(SI_{ps})} \quad \text{(Equation 5)}$$

Figure 10:
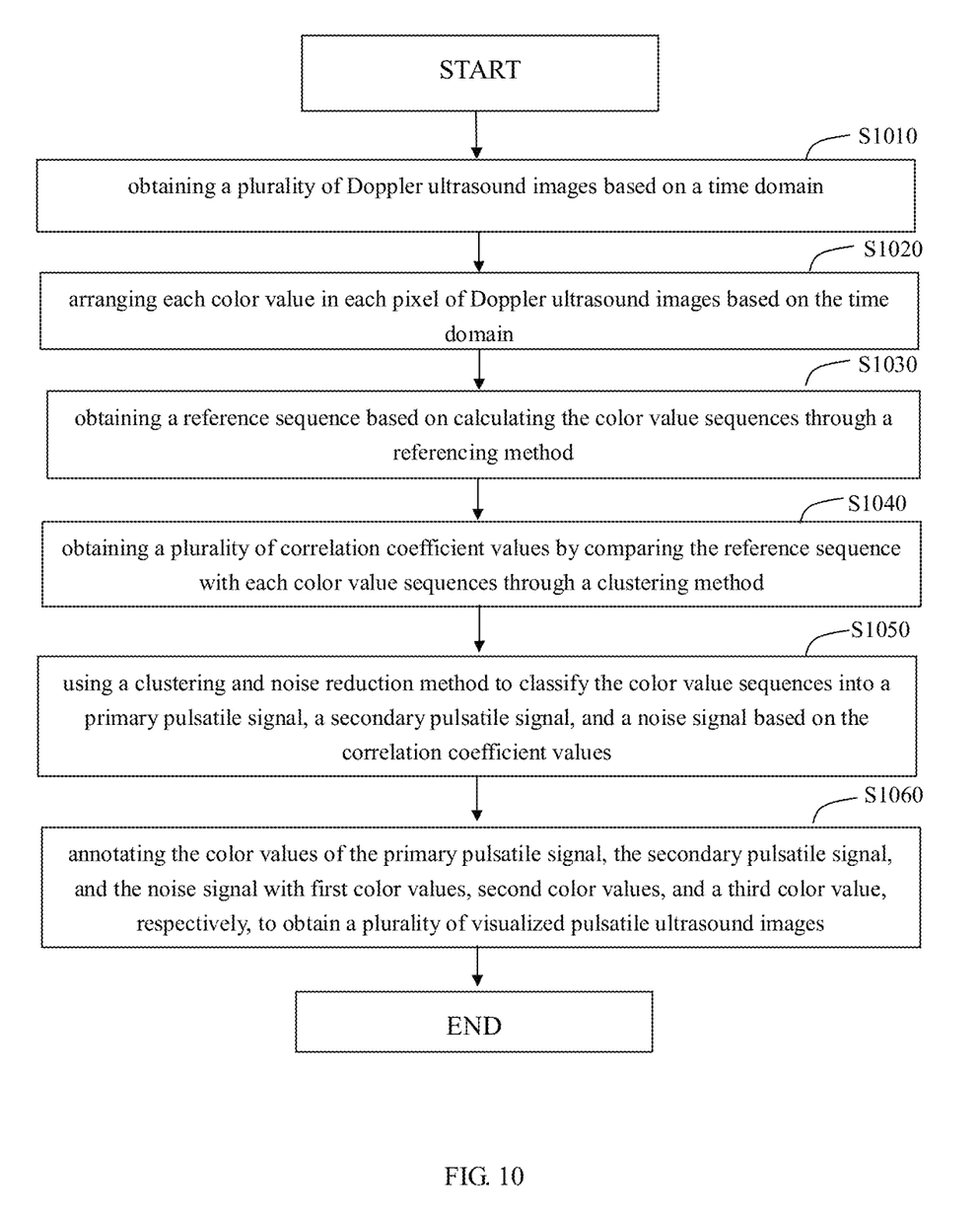
FIG. 10 is a flowchart for the method of clustering, noise reduction and visualization for Doppler ultrasound images according to various embodiments of the present invention.

FIG. 10 is a flowchart for the method of clustering, noise reduction and visualization for Doppler ultrasound images according to various embodiments of the present invention. It should be noted that the flowchart of FIG. 10 provides merely an example of the many different types of functional arrangements that may be employed to implement the operation of the various components of the image processing system 100 (FIG. 1). As an alternative, the flowchart of FIG. 10 may be viewed as depicting an example of steps of a method implemented in the image processing system 100 according to one or more embodiments.

Although the flowchart of FIG. 10 shows a specific order of execution, it should be noted that the order of execution may differ from that which is depicted. For example, the order of execution of two or more blocks may be scrambled relative to the order shown. Also, two or more blocks shown in succession in FIG. 10 may be executed concurrently or with partial concurrence. It should be noted that all such variations are within the scope of the present invention.

Beginning with step S1010, a sequence of Doppler ultrasound images (I frames) 210 based on a time domain are obtained, wherein each Doppler ultrasound image comprises a color value in each pixel ($B_{j,i}$).

In step S1020, each color value in each pixel of the Doppler ultrasound images are arranged based on the time domain to obtain a plurality of color value sequences.

In step S1030, a reference sequence ($C_{ref}$) is obtained through a referencing method. The referencing method comprises an intensity percentage method, an average standard deviation ratio method, an autocorrelation method, a hierarchical correlation method or any combination thereof.

In step S1040, the data analysis processor 124 compares the reference sequence with each color value sequence through a clustering method to obtain a plurality of correlation coefficient values. The clustering method comprises a correlation grouping method, a grouping with lag-correlation method, a two-centers correlation clustering method or any combination thereof.

In step S1050, the data analysis processor 124 further performs a clustering and noise reduction method to classify the color value sequences into a primary pulsatile signal, a secondary pulsatile signal, and a noise signal based on the correlation coefficient values.

Finally, in step S1060, the data record processor 126 annotates the color value in each pixel which belong to the primary pulsatile signal, the secondary pulsatile signal, and the noise signal with different color values to obtain a plurality of visualized pulsatile ultrasound images.

In addition to the aforesaid steps, the method of clustering, noise reduction and visualization for Doppler ultrasound images of the present invention can also execute all the operations and have all the corresponding functions set forth in all the aforesaid embodiments. How this embodiment executes these operations and has these functions will be readily appreciated by those of ordinary skill in the art based on the explanation of all the aforesaid embodiments, and thus will not be further described herein.

According to the above descriptions, the system and the method of clustering, noise reduction and visualization for Doppler ultrasound images of the present invention provide the Doppler ultrasound images with different colors to visually segment the primary pulsatile signal, the secondary pulsatile signal, and the noise signal in consideration that signal intensities of Doppler ultrasound images would be affected by pulsatile flow intensities of the artery and the vein. Therefore, the method and system in this invention can apply different appropriate analysis methods on different specific organs, respectively, to visualize information of the artery and the vein and reduce the noise caused by the motion artifacts to clearly present the artery and the vein, thereby improving diagnostic accuracy and efficiency.

It shall be appreciated that the method and system do not limit to blood signal of the specific organ and utilizes one of the clustering methods, for example, the correlation grouping method, the two-center correlation clustering method, and hierarchical correlation clustering method to obtain the Doppler ultrasound images for different organs. It should be emphasized that the above-described embodiments of the present invention are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A system of clustering, noise reduction and visualization for Doppler ultrasound image, comprising:
   a capture device, being configured to obtain a plurality of Doppler ultrasound images based on a time domain, wherein each of the Doppler ultrasound image comprises a color value in each pixel;
   a processing device, being connected to the capture device, and comprising:
   a data conversion processor, being configured to arrange the color value in each pixel of the Doppler ultrasound images based on the time domain to obtain a plurality of color value sequences;
   a data analysis processor, being configured to calculate the color value sequences through a referencing method to obtain a reference sequence, compare the reference sequence with each of the color value sequences through a clustering method to obtain a plurality of correlation coefficient values, and classify the color value sequences into a primary pulsatile signal, a secondary pulsatile signal, and a noise signal based on the correlation coefficient values through a clustering and noise reduction method; and
   a data record processor, being configured to annotate the color values of the primary pulsatile signal, the secondary pulsatile signal, and the noise signal to obtain a plurality of visualized pulsatile ultrasound images;
   an output device, being connected to the processing device and configured to display the visualized pulsatile ultrasound images.

2. The system of claim 1, wherein the output device provides selection of a region of interest in the visualized pulsatile ultrasound images, the data record processor obtains a plurality of intensity value change trends of the primary pulsatile signal, the secondary pulsatile signal, and the noise signal in the region of interest of the visualized pulsatile ultrasound images by following steps:
   normalizing the color values of each pixel of the primary pulsatile signal, the secondary pulsatile signal, and the noise signal in the region of interest of the visualized pulsatile ultrasound image;
   calculating an average of the normalized color values of the primary pulsatile signal at each capture time to obtain a plurality of intensity value of the primary signal;
   calculating an average of the normalized color values of the secondary pulsatile signal at each capture time to obtain a plurality of intensity values of the secondary pulsatile signal; and
   calculating an average of the normalized color values of the noise signal at each capture time to obtain a plurality of intensity values of the noise signal;
   wherein the output device further displays a plurality of intensity value change trends in a chart according to the intensity values of the primary signal, the secondary pulsatile signal, and the noise signal.

3. The system of claim 2, wherein the output device calculates a plurality of first similarity indices between the intensity value change trend of the primary pulsatile signal and the intensity value change trend of the secondary pulsatile signal, a plurality of second similarity indices between the intensity value change trend of the primary signal and the intensity value change trend of the noise signal, and a plurality of third similarity indices similarity indices between the intensity value change trend of the secondary signal and the intensity value change trend of the noise signal through a correlation function with a plurality of lag varieties, and the output device chooses a largest value from the first similarity indices to be a pulsatile similarity index, chooses the largest value from the second and third similarity indices to be the noise similarity index, and obtains a ratio coefficient by dividing the noise similarity index by the pulsatile similarity index .

4. The system of claim 1, wherein the referencing method is an intensity percentage method, the data analysis processor performs the intensity percentage method to obtain the reference sequence, and the intensity percentage method comprises the following steps of:
   arranging the color value sequences according to the largest color value of each of the color value sequences to obtain a plurality of percentile ranks;
   choosing the color value sequences which the percentile rank is within a predetermined rank range to obtain a reference group; and
   averaging the color value sequences in the reference group to obtain the reference sequence.

5. The system of claim 1, wherein the referencing method is an average standard deviation ratio method, the data analysis processor performs the average standard deviation ratio method to obtain the reference sequence, and the average standard deviation ratio method comprises the following steps of:
   calculating the color value in each color value sequences to obtain a plurality of standard deviation values, and then dividing by an average value of the standard deviation values to obtain a plurality of average standard deviation ratio values;
   choosing the color value sequences which the averaging standard deviation ratio value is within a predetermined ratio range to obtain a reference group; and averaging the color value sequences in the reference group to obtain the reference sequence.

6. The system of claim 1, wherein the referencing method is an autocorrelation method, the data analysis processor performs the autocorrelation method to obtain the reference sequence, and the autocorrelation method comprises the following steps of:
calculating each color value sequence through an autocorrelation function with a plurality of lag varieties to obtain a plurality of autocorrelation coefficient values; and
choosing a color value sequence which has the smallest autocorrelation coefficient value to obtain the reference sequence.

7. The system of claim 1, wherein the referencing method is a hierarchical correlation method, the data analysis processor performs the hierarchical correlation method to obtain the reference sequence, and the hierarchical correlation method comprises the following steps of:
(a) gathering the color value sequences into an $i^{th}$ reference sequence set, wherein an initial value of i is 1;
(b) obtaining a plurality of correlation coefficient values of the $i^{th}$ reference sequence set by calculating each pair of the color value sequences in the $i^{th}$ reference sequence set through a correlation function;
(c) selecting the pair of the color value sequences in the $i^{th}$ reference sequence set, which have a largest correlation coefficient value;
(d) averaging the selected pair of the color value sequences in the $i^{th}$ reference sequence set to generate a new color value sequence;
(e) gathering the new color value sequence and the color value sequences in the $i^{th}$ reference sequence set except for the selected pair of the color value sequences into a $(i+1)^{th}$ reference sequence set;
(f) obtaining a plurality of correlation coefficient values of the $(i+1)^{th}$ reference sequence set by calculating each pair of the color value sequences in the $(i+1)^{th}$ reference sequence set through the correlation function;
(g) determining whether all of the correlation coefficient values of the $(i+1)^{th}$ reference sequence set are less than a predetermined correlation threshold; and
(h) when one of the correlation coefficient values of the $(i+1)^{th}$ reference sequence set is not less than the predetermined correlation threshold, setting i=i+1 and repeating steps (c), (d), (e), (f) and (g), and when the all of the correlation coefficient values of the $(i+1)^{th}$ reference sequence set are less than the predetermined correlation threshold, outputting the color value sequence in the $(i+1)^{th}$ reference sequence set which is generated by averaging a most number of the color value sequences in the first reference sequence set as a reference sequence.

8. The system of claim 1, wherein the clustering method is a correlation grouping method, the data analysis processor performs the correlation grouping method to obtain the correlation coefficient values, and the correlation grouping method comprises the following step of:
calculating each of the color value sequences with the reference sequence through a correlation function to obtain the correlation coefficient values of the color value sequences.

9. The system of claim 1, wherein the clustering method is a two-centers correlation clustering method, the data analysis processor performs the two-centers correlation clustering method to obtain the correlation coefficient values, and the two-centers correlation clustering method comprises the following steps of:
(a) gathering the color value sequences into an operation set;
(b) calculating each of the color value sequences in the operation set with the reference sequence through a correlation function to obtain a plurality of temporary correlation coefficient values of the color value sequences;
(c) removing the color value sequence with the smallest temporary correlation coefficient value from the operation set and assigning the smallest temporary correlation coefficient value to be the correlation coefficient value of the color value sequence with the smallest temporary correlation coefficient value;
(d) removing the color value sequence with the largest temporary correlation coefficient value and assigning the largest temporary correlation coefficient value to be the correlation coefficient value of the color value sequence with the largest temporary correlation coefficient value;
(e) updating the reference sequence by averaging the color value sequence with the largest temporary correlation coefficient value and the reference sequence; and
(f) repeating steps (b), (c), (d), and (e) until all of the color value sequences are assigned with the correlation coefficient values.

10. The system of claim 1, wherein the clustering method is a grouping with lag-correlation method, the data analysis processor performs the grouping with lag-correlation method to obtain the correlation coefficient values, and the grouping with lag-correlation method comprises the following steps of:
calculating each color value sequences with the reference sequence through a correlation function with a plurality of lag varieties to obtain a plurality of correlation coefficient values;
choosing the largest correlation coefficient value and the corresponding lag variety to obtain the correlation coefficient value and the lag variety of each color value sequence.

11. The system of claim 1, wherein the data analysis processor further compares the reference sequence with each of the color value sequences through the clustering method to obtain the correlation coefficient values and a plurality of lag varieties corresponding to the correlation coefficient values of the color value sequences and performs the clustering and noise reduction method comprising the following steps of:
classifying the color value sequences, the correlation coefficient values of which are within a main correlation coefficient threshold and the lag varieties of which are within a main lag-coefficient threshold, into the primary pulsatile signal;
classifying the color value sequences, the correlation coefficient values of which are within a secondary correlation coefficient threshold and the lag varieties of which are within a secondary lag-coefficient threshold, into the secondary pulsatile signal; and
classifying the color value sequences, the correlation coefficient values of which are not within the main correlation coefficient threshold and the secondary correlation coefficient threshold and the lag variety of which are not within the main lag-coefficient threshold and the secondary lag-coefficient threshold, into the noise signal.

12. The system of claim 1, wherein the step of obtaining the visualized pulsatile ultrasound images executed by the data record processor comprises the following steps of:

for each of the visualized pulsatile ultrasound images:
selecting a pixel of the noise signal as a center pixel of a mask region;
calculating a number of pixels in the mask region;
reclassifying the noise signal into the primary pulsatile signal if the number of primary pulsatile signals is more than that of the secondary pulsatile signals in the mask region; and
reclassifying the noise signal into the secondary pulsatile signal if the number of secondary pulsatile signals is more than that of the primary pulsatile signals in the mask region.

13. The system of claim 1, wherein the step of obtaining the visualized pulsatile ultrasound images executed by the data record processor, further comprises the following steps of:

annotating the pixels which belong to the primary pulsatile signal with first color values;
annotating the pixels which belong to the secondary pulsatile signal with second color values;
annotating the pixels which belong to the noise signal with a third color value; and
obtaining the visualized pulsatile ultrasound images.

14. A method of clustering, noise reduction and visualization for Doppler ultrasound image, comprising:

obtaining a plurality of Doppler ultrasound images based on time domain, wherein each of Doppler ultrasound images comprises a color value in each pixel;
arranging each color value in each pixel of Doppler ultrasound images based on the time domain to obtain a plurality of color value sequences;
calculating the color value sequences through a referencing method to obtain a reference sequence;
comparing the reference sequence with each color value sequences through a clustering method to obtain a plurality of correlation coefficient values;
classifying the color value sequences into a primary pulsatile signal, a secondary pulsatile signal, and a noise signal based on the correlation coefficient values through a clustering and noise reduction method; and
annotating the color values of the primary pulsatile signal, the secondary pulsatile signal, and the noise signal with first color values, second color values, and a third color value, respectively, to obtain a plurality of visualized pulsatile ultrasound images.

* * * * *